United States Patent [19]

Uzuka et al.

[11] Patent Number: 4,963,588

[45] Date of Patent: Oct. 16, 1990

[54] USE OF UBENIMEX FOR TREATING MYELODYSPLASTIC SYNDROME

[75] Inventors: Yoshiro Uzuka; Yoshiko Saito, both of Sendai, Japan

[73] Assignee: Nippon Kayaku Kabushiki Kaisha, Tokyo, Japan

[21] Appl. No.: 462,822

[22] Filed: Jan. 10, 1990

[30] Foreign Application Priority Data

Feb. 23, 1989 [JP] Japan .................................. 1-41630

[51] Int. Cl.$^5$ ........................................... A61K 31/195
[52] U.S. Cl. ................................................... 514/563
[58] Field of Search ........................................ 514/563

[56] References Cited

U.S. PATENT DOCUMENTS 4,189,604 2/1980 Umezawa et al. .................. 562/437
4,281,180 7/1981 Umezawa et al. .................. 562/448

OTHER PUBLICATIONS

"Cancer Chemotherapy," vol. 7, pp. 76–82, Elsevier, Amsterdam (1985).

"Recent Results of Bestatin 1985—A Biological Response Modifier–," pp. 1–12, Japan Antibiotics Research Association, Tokyo (1985).

*Primary Examiner*—Jerome D. Goldberg
*Attorney, Agent, or Firm*—Henry C. Nields

[57] ABSTRACT

This invention relates to a use of ubenimex or a pharmacologically acceptable salt thereof for treating myelodysplastic syndrome (MDS).

1 Claim, No Drawings

USE OF UBENIMEX FOR TREATING MYELODYSPLASTIC SYNDROME

BACKGROUND OF THE INVENTION

It is known that ubenimex (INN) inhibits aminopeptidase B (cf. U.S.P. No. 4,189,604) and has a antitumor activities (cf. Japanese Pat. Publication (A2) No. 9487/1985) as well as a low toxicity. It has already been put into commercial use under a tradename of Bestatin ®.

Myelodysplastic syndrome, which will be referred to simply MDS hereinafter, is mainly observed among aged people in high frequently. It causes dysplastic hematopoiesis and refractory to common hematopoietics. It is apt to transform to acute leukemia, or it frequently induces death due to serious infectious diseases, anemia or hemorrhage caused by dysfunction of blood cells. At present no standard therapy is established and several attempts are being made to treat this disease by using some adrenocortical hormones, androgen, hematopoietic vitamins, Ara-C and its derivatives or interferon γ. However, no satisfactory therapeutic effects is obtained with these drugs. Thus it has been desired to develop an more effective remedy for MDS, in particular for high blast types, refractory anemia with excess of blast (RAEB) and RAEB in transformation (RAEB-t).

SUMMARY OF THE INVENTION

As the result of extensive studies, the present inventors have found that N-[(2S, 3R)-3-amono-2-hydroxy-4-phenylbutyryl]-(L)-leucine (nonproprietary name: ubenimex) or its salt is highly effective in the treatment of MDS, thus completing the present invention.

DETAILED DESCRIPTION OF THE INVENTION

Accordingly, the present invention relates to a remedy for MDS comprising ubenimex or its salt as an active ingredient.

The remedy for MDS of the present invention is effective in the treatment of not only MDS of high blast types but also that of low blast type with prolonged good prognosis.

Ubenimex can form salts with any acid or base and any of them may be used in the present invention, so long as it is pharmacologically acceptable. Examples of such ubenimex salt with an acid include hydrochloride, sulfate and phosphate.

When ubenimex is to be used as a remedy for MDS, it may be administered to patient in the form of, for example, an injection, an oral drug or a suppository either alone or together with pharmaceutical additives such as additives or carriers. The additives and carriers may be selected from among pharmaceutically acceptable ones and the kind and composition thereof may be appropriately determined depending on the route and method of the administration.

Examples of liquid additives and carriers include water, alcohols, soybean oil, peanut oil, rubber oil, mineral oil and other vegetable, animal and synthetic oils. Examples of solid additives and carriers include sugars such as maltose and sucrose, amino acids, cellulose derivatives such as hydroxypropylcellulose, starches such as potato starch and organic acid salts such as magnesium stearate. When the remedy of the present invention is to be formulated into an injection, physiological saline solution, various buffers, solutions of sugars such as glucose, inositol and mannitol and glycols such as ethylene glycol and polyethylene glycol are preferably employed in general. Alternately, it may be lyophilized together with various additives, for example, sugars such as inositol, mannitol, glucose, mannose, maltose or sucrose or amino acids such as phenylalanine. The lyophilized preparation thus obtained may be reconstituted with a solvent suitable for intravenous injection, for example, sterilized water, physiological saline solution, a glucose solution, an electrolyte solution or an amino acid solution at the administration.

The content of the active ingredient of the present invention in a preparation may vary depending on the formulation method. It generally ranges from 0.01 to 100% by weight, preferably 0.02 to 90% by weight.

When the remedy of the present invention is to be orally administered, it may be formulated into, for example, a tablet, a capsule, a powder, a granule, a solution or a dry syrup together with the above-mentioned solid or liquid carrier(s). The capsule, tablet, granule or powder may contain approximately 0.02 to 90% by weight, preferably 0.3 to 20% by weight, of ubenimex with the carrier(s) of approximately 99.98 to 10% by weight, preferably about 99.7 to 80% by weight.

The dose of the compound of the present invention may vary depending on, for example, the age, body weight and symptom of the patient and the purpose of the treatment. Usually, the therapeutic dose for adults is parenterally 1 to 300 mg/day or orally 5 to 500 mg/day.

Ubenimex is characterized by its low toxicity and low accumulated toxicity upon repeated administration. The following table shows the acute toxicity of ubenimex for reference.

| 1. Acute toxicity ($LD_{50}$ g/kg) | | | | |
|---|---|---|---|---|
| Animal | | Administration method | | |
| Species | Sex | Oral | Sub-cutaneous | Intra-peritoneal |
| Mouse (ICR) | ♂ | >4.0* | 1.3 | 0.19 |
|  | ♀ | >4.0* | 1.9 | 0.19 |
| Rat (SD) | ♂ | >2.0* | 1.9 | 0.90 |
|  | ♀ | >2.0* | 2.1 | 0.78 |
| Beagle | ♂ | >1.2* | — | — |

Note: *means the maximum administration level.

COMPOSITION EXAMPLE 1

20 Parts of ubenimex, 77 parts of potato starch, 100 parts of crystalline, lactose and 3 parts of magnesium stearate were mixed homogeneously. Thus obtained mixture (about 220mg per a capsule) was packed into a capsule of No.3 to give a capsule preparation of this invention.

COMPOSITION EXAMPLE 2

Purified water was added to 30 parts by weight of ubenimex and the total volume was adjusted to 2,000 parts. After complete dissolution, the resulting solution was sterilized by filtering it through Millipore filter of GS type. Two grams of the filtrate was taken into a 10ml vial and freeze-dried. Thus, a freeze-dried injection containing 30mg of Compound (1) per one vial was obtained.

COMPOSITION EXAMPLE 3: GRANULE

50 Parts by weight of ubenimex, 600 parts of lactose, 330 parts of crystalline cellulose and 20 parts of hydroxypropyl cellulose were mixed and thoroughly homogenized, pressed by means of roll type press (Roller Compactor®), crushed, and sieved. The fraction between 16 meshes and 60 meshes was taken and used as granule.

COMPOSITION EXAMPLE 4: TABLET

30 Parts by weight of ubenimex, 120 parts of crystalline lactose, 147 parts of crystalline cellulose and 3 parts of magnesium stearate were mixed homogeneously, formed into tablet by means of V-type blender. Thus a tablet of 300mg was obtained. Treatment response by ubenimex against MDS are illustrated by following test examples

TEST EXAMPLE

The capsule of ubenimex prepared by the composition example 1 was orally administered 30mg/day to seven RAEB or RAEB-T patients aged between 49 and 72. After administration, its response was observed.

Good results were observed in six patients except one. The good results in six are shown in the following table.

EFFECTS OF THE INVENTION

As is apparent from these tables, one RAEB-T case and three RAEB cases showed complete remission and two RAEB cases showed good responses among six effective cases. Thus it has been proved that ubenimex is highly effective as a remedy for MDS since it can
  (1) improve cytopenia (such as anemia, thrombocytopenia and neutropenia),
  (2) reduce excess blast,
  (3) improve myelodysplasia and as the result of these effects, the amount of transfusion to the patients is reduced or sometimes become unnecessary and improvement of prognosis of the patient is expected.

We claim:

1. A method for treating myelodysplastic syndrome (MDS) in human having MDS which comprises administering ubenimex or a pharmacologically acceptable salt thereof in an effective amount to said human for treating myelodysplastic syndrome.

* * * * *

| | | | | Peripheral blood | | | | | | | | | | Days till | |
| | | | | Granulocytes ($\times 10^9/l$) | | Platelets No. ($\times 10^9/l$) | | Hemoglobin (g/dl) | | Bone marrow | | | | | |
| | Patient | | | | | | | | | Myelodysplasia | | Blast (%) | | Re- | response | Duration of response |
| NO | Age | Sex | Symptom | BT* | AT* | BT | AT | BT | AT | BT | AT | BT | AT | sponse | (day) | (week) |
|---|---|---|---|---|---|---|---|---|---|---|---|---|---|---|---|---|
| 1 | 49 | ♂ | RAEB-T | 1.11 | 2.94 | 350 | 372 | 10.5 | 13.6 | + | − | 22.8 | 3.2 | CR* | 34 | 8 (observation continued) |
| 2 | 67 | ♂ | RAEB | 0.62 | 2.44 | 81 | 209 | 7.9 | 14.4 | + | − | 13.2 | 5.2 | CR | 28 | 11 (ubenimex administration suspended) |
| 3 | 73 | ♀ | " | 0.99 | 1.75 | 12 | 96 | 6.8 | 12.3 | + | − | 5.2 | 0.4 | CR | 97 | 21 (observation continued) |
| 4 | 52 | ♂ | " | 2.92 | 2.35 | 30 | 82 | 7.6 | 11.0 | + | − | 6.0 | 2.0 | CR | 175 | 28 (observation) continued) |
| 5 | 73 | ♀ | " | 1.22 | 2.44 | 21 | 176 | 8.5 | 8.7 | + | | 7.8 | | GR* | 134 | 32 (observation continued) |
| 6 | 73 | ♀ | " | 1.45 | 2.02 | 42 | 186 | 10.9 | 12.2 | + | | 10.8 | | GR | 67 | 20 (observation continued) |

Note:
*BT: before treatment;
AT: after treatmetn;
CR: complete remission; and
GR: good result.